US012629142B2

(12) United States Patent
Chen et al.

(10) Patent No.: US 12,629,142 B2
(45) Date of Patent: May 19, 2026

(54) OCCLUDER

(71) Applicant: SHANGHAI SHAPE MEMORY ALLOY CO., LTD, Shanghai (CN)

(72) Inventors: Juan Chen, Shanghai (CN); Fan Wang, Shanghai (CN); Yunbing Wang, Shanghai (CN); Jinpeng Hu, Shanghai (CN); Dezhong Liu, Shanghai (CN); Xiangbin Pan, Shanghai (CN)

(73) Assignee: SHANGHAI SHAPE MEMORY ALLOY CO., LTD, Shanghai (CN)

( * ) Notice: Subject to any disclaimer, the term of this patent is extended or adjusted under 35 U.S.C. 154(b) by 14 days.

(21) Appl. No.: 18/852,765

(22) PCT Filed: Apr. 3, 2023

(86) PCT No.: PCT/CN2023/085930
§ 371 (c)(1),
(2) Date: Sep. 30, 2024

(87) PCT Pub. No.: WO2023/186172
PCT Pub. Date: Oct. 5, 2023

(65) Prior Publication Data
US 2025/0221695 A1     Jul. 10, 2025

(30) Foreign Application Priority Data
Apr. 1, 2022    (CN) .......................... 202210348691.9

(51) Int. Cl.
*A61B 17/00* (2006.01)
(52) U.S. Cl.
CPC ................................ *A61B 17/0057* (2013.01); *A61B 2017/00588* (2013.01); *A61B 2017/00597* (2013.01);
(Continued)

(58) Field of Classification Search
CPC ...... A61B 17/0057; A61B 2017/00575; A61B 2017/00606; A61B 2017/00632;
(Continued)

(56) References Cited

U.S. PATENT DOCUMENTS 5,709,707 A     1/1998 Lock et al.
9,375,209 B2    6/2016 Akpinar
(Continued)

FOREIGN PATENT DOCUMENTS

CN     201082203 Y     7/2008
CN     103945774 A     7/2014
(Continued)

OTHER PUBLICATIONS

First Office Action of corresponding CN application CN202210348691.9, dated Oct. 29, 2024, pp. 1-16 in pdf including English translation.
(Continued)

*Primary Examiner* — Majid Jamialahmadi
(74) *Attorney, Agent, or Firm* — EVENTIDE LAW LLC

(57) ABSTRACT

The present application discloses an occluder, including a distal disc, a waist portion, and a proximal disc which are formed in sequence. The proximal disc includes a proximal disc surface. A proximal bending area is formed at a circumference of the proximal disc surface and bent towards the distal disc, where the proximal bending area surrounds an edge of the distal disc, and a stabilizing wire is further threaded through a free end of the proximal bending area and may tighten the free end of the proximal bending area towards the waist portion.

15 Claims, 4 Drawing Sheets

(52) U.S. Cl.
     CPC ................ *A61B 2017/0061* (2013.01); *A61B 2017/00632* (2013.01); *A61B 2017/00659* (2013.01)

(58) Field of Classification Search
     CPC .. A61B 2017/00592; A61B 2017/2918; A61B 2017/00597
     See application file for complete search history.

(56) References Cited

U.S. PATENT DOCUMENTS

| | | | |
|---|---|---|---|
| 10,278,705 | B2 | 5/2019 | Amin et al. |
| 2002/0169475 | A1 | 11/2002 | Gainor et al. |
| 2007/0179527 | A1 | 8/2007 | Eskuri et al. |
| 2012/0071918 | A1 | 3/2012 | Amin et al. |
| 2014/0039543 | A1* | 2/2014 | Willems ............. A61B 17/0057 606/200 |
| 2021/0059651 | A1 | 3/2021 | Gutfinger et al. |
| 2022/0257259 | A1 | 8/2022 | Li et al. |
| 2022/0346803 | A1* | 11/2022 | Wang ................. A61B 17/0057 |
| 2023/0210537 | A1 | 7/2023 | Li et al. |
| 2023/0277166 | A1 | 9/2023 | Chen et al. |

FOREIGN PATENT DOCUMENTS

| | | | |
|---|---|---|---|
| CN | 204636434 | U | 9/2015 |
| CN | 204971422 | U | 1/2016 |
| CN | 105433991 | A | 3/2016 |
| CN | 107397562 | A | 11/2017 |
| CN | 207627356 | U | 7/2018 |
| CN | 111297412 | A | 6/2020 |
| CN | 211325298 | U | 8/2020 |
| CN | 111956275 | A | 11/2020 |
| CN | 112656474 | A | 4/2021 |
| CN | 112998769 | A | 6/2021 |
| CN | 113576585 | A | 11/2021 |
| CN | 113813039 | A | 12/2021 |
| CN | 215018260 | U | 12/2021 |
| CN | 215384308 | U | 1/2022 |
| DE | 102005053957 | A1 | 5/2007 |
| EP | 2617386 | B1 | 10/2017 |
| WO | 2021185127 | A1 | 9/2021 |

OTHER PUBLICATIONS

International Search Report of corresponding PCT application (PCT/CN2023/085930), dated Jul. 14, 2023, pp. 1-6.

Written Opinion of International Searching Authority of corresponding PCT application (PCT/CN2023/085930), dated Jul. 14, 2023, pp. 1-13.

Extended European Search Report for European Application No. 23778536.5, dated Jan. 15, 2026, pp. 1-8.

* cited by examiner

OCCLUDER

FIELD

The present invention relates to the technical field of medical devices, and particularly to an occluder.

BACKGROUND

The foramen ovale in the fetal period serves as a physiological channel for blood to flow from the right atrium to the left atrium, maintaining fetal blood circulation. The foramen ovale typically closes 5 to 7 months after birth as the pulmonary circulation is established and as the left atrial pressure increases. If, after the age of 3, the septum secundum and septum primum at the fossa ovalis have not fully fused, leaving an oblique defect in the middle, it is referred to as patent oval foramen (PFO). Approximately 20%-40% of adults have an incompletely closed foramen ovale, leaving a small gap. Currently, for abnormal embolism or unexplained stroke caused by the PFO, interventional occlusion therapy is the preferred therapy solution.

Currently, most of the occluders used for the interventional therapy on the market are made of nickel-titanium alloy, which has good shape memory properties. However, the nickel-titanium alloy material is non-degradable after being implanted in the human body and carries the risk of metal ion leaching. The biodegradable occluder is a new type of occluder product that can effectively occlude the cardiac defect while being biodegradable within a suitable time. The degradation products can be completely metabolized by the human body, leaving no residual materials after the cardiac defect has been repaired. Therefore, the degradable occluder is the development trend. However, because the mechanical properties of degradable materials cannot reach those of the metal materials, the compliance and recovery of the prepared occluder are poor. Thus, after the occluder is released, the left and right discs cannot fit well to the left and right sides of the cardiac septal defect position, resulting in a poor occluding effect and even causing a risk of residual blood shunts. Additionally, when the occluder cannot fit well to the cardiac septal tissue, it is difficult for endothelial cells to adhere and cover the occluder, resulting in an unsatisfactory process of endothelialization in the short term and long term after the occluder is implanted.

SUMMARY

It is an object of embodiments of the present invention to overcome the disadvantages described in the related art and to provide an occluder which features good stability, resistance to deformation, and close fit to the interatrial septum after implantation, thus facilitating endothelialization. The specific technical solutions are as follows.

An occluder is provided, including a distal disc, a waist portion and a proximal disc formed in sequence;

the proximal disc includes a proximal disc surface, a proximal bending area bent toward the distal disc is formed at a circumference of the proximal disc surface, and wherein the proximal bending area surrounds an edge of the distal disc, and a stabilizing wire is further threaded through a free end of the proximal bending area and able to tighten the free end of the proximal bending area towards the waist portion.

Optionally, a diameter of the proximal disc is greater than a diameter of the distal disc, and the distal disc includes a distal disc surface, a distal bending area arranged opposite to the proximal bending area is formed at a circumference of the distal disc surface, and a free end of the distal bending area extends into the proximal bending area. Optionally, the proximal bending area includes a proximal outer cambered surface extending from the circumference of the proximal disc surface, a distance between an inner end of the proximal outer cambered surface and an axis of the waist portion is less than a distance between an outer end of the proximal outer cambered surface and the axis of the waist portion, and the stabilizing wire is threaded through the outer end of the proximal outer cambered surface.

Optionally, the proximal bending area bulges away from the distal disc and includes a proximal inner cambered surface, a proximal bending arc and the proximal outer cambered surface connected in sequence, an inner end of the proximal inner cambered surface is connected to the proximal disc surface, and the stabilizing wire is threaded through the outer end of the proximal outer cambered surface, the distance between the inner end of the proximal outer cambered surface and the axis of the waist portion is less than the distance between the outer end of the proximal outer cambered surface and the axis of the waist portion.

Optionally, a supplementary angle $\alpha$ of an included angle between the proximal outer cambered surface and the proximal disc surface is in a range of greater than 90 degrees and less than 170 degrees.

Optionally, when the stabilizing wire tightens the proximal bending area, an arc of the proximal bending arc is less than or equal to 90 degrees, and the supplementary angle $\alpha$ of the included angle between the proximal outer cambered surface and the proximal disc surface is in a range of greater than 90 degrees and less than 160 degrees.

Optionally, a projected length of the proximal outer cambered surface in an axial direction of the proximal disc surface is greater than or equal to 1 mm, and a projected length of the proximal outer cambered surface in a radial direction of the proximal disc surface is less than a half of the diameter of the proximal disc.

Optionally, the distal bending area includes a distal outer cambered surface extending from the circumference of the distal disc surface, a distance between an inner end of the distal outer cambered surface and the axis of the waist portion is less than the distance between the outer end of the proximal outer cambered surface and the axis of the waist portion, and the stabilizing wire is threaded through the outer end of the distal outer cambered surface.

Optionally, the distal bending area is bent towards the proximal disc and protrudes, including a distal inner cambered surface, a distal bending arc and the distal outer cambered surface extending from the circumference of the distal disc surface in sequence, a distance between an inner end of the distal outer cambered surface and the axis of the waist portion is greater than a distance between an outer end of the distal outer cambered surface and the axis of the waist portion, and the free end of the distal outer cambered surface extends into the proximal bending area.

Optionally, a supplementary angle $\beta$ of an included angle between the distal outer cambered surface and the distal disc surface is in a range of greater than 90 degrees and less than 170 degrees.

Optionally, when a stabilizing wire tightens the distal bending area, an arc of the distal bending arc is less than or equal to 90 degrees, and the included angle between the distal outer cambered surface and an extension surface of the distal disc surface is in a range of greater than 90 degrees and less than 160 degrees;

3 a projected length of the distal outer cambered surface in an axial direction of the distal disc surface is greater than or equal to 1 mm, and a projected length of the distal outer cambered surface in a radial direction of the distal disc surface is less than a half of the diameter of the distal disc.

Optionally, a stabilizing wire is also threaded through the free end of the distal bending area, and the stabilizing wire includes one or more loops.

Optionally, an inner wall of the distal disc, an inner wall of the proximal disc, and a position between the proximal disc and the distal disc are covered with flow blocking membranes.

Optionally, the proximal disc, the waist portion, and the distal disc are all made of degradable wires, and the occluder is further provided with a developing mark.

Optionally, the developing mark is a platinum wire or a platinum ring.

The technical solutions provided by the present invention have at least the following beneficial effects.

In the present application, the proximal disc is provided with two regions, i.e., the proximal disc surface and the proximal bending area. The proximal disc surface relatively forms a subsidence area, and the proximal bending area is provided as a part mainly used for providing a locking force so that the recovering effect of the shape of the proximal disc surface may be increased. Specifically, the bending area formed by the proximal bending area may increase a fitting length of the proximal disc to a tissue surface, enhance the fitting and occluding effect, promote rapid endothelialization, and avoid residual shunts. The stabilizing wire is provided so that the proximal bending area may provide a centripetal force to the septal tissue, ensuring that the occluder can stably maintain the design shape and size for a long time after implantation, thereby always fitting to the interatrial septum stably. Meanwhile, the buckling and surrounding pattern of the proximal bending area of the proximal disc to the distal disc may further ensure that the occluder can clamp and fit the septal tissue after implantation.

BRIEF DESCRIPTION OF THE DRAWINGS

In order to more clearly illustrate the technical solutions in the embodiments of the present invention, the drawings required in the description of the embodiments will be briefly introduced below. Obviously, the drawings described below are only some embodiments of the present invention, and a person skilled in the art may obtain other drawings according to these drawings without involving any inventive effort.

4

Figure 7:
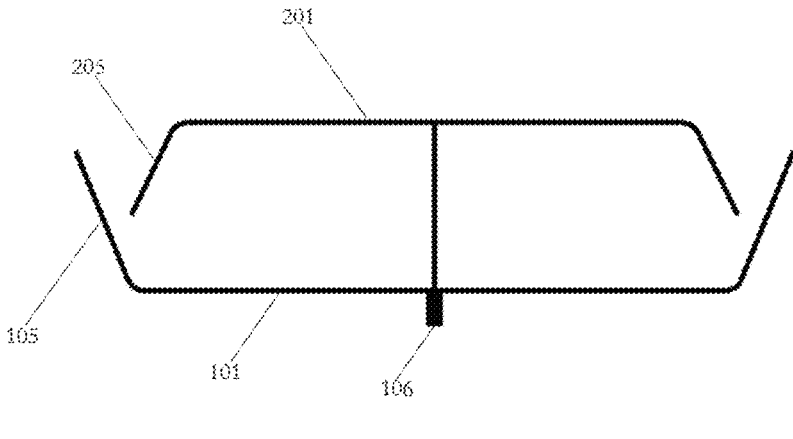

FIG. 7 is an outline schematic diagram of an occluder according to another embodiment of the present invention.

DESCRIPTION OF REFERENCE NUMERALS

100—proximal disc; 101—proximal disc surface; 102—proximal bending area; 103—proximal inner cambered surface; 1031—inner end of proximal inner cambered surface; 1032—outer end of proximal inner cambered surface; 104—proximal bending arc; 105—proximal outer cambered surface; 1051—inner end of proximal outer cambered surface; 1052—outer end of proximal inner cambered surface; and 106—fixing rivet;

200—distal disc; 201—distal disc surface; 202—distal bending area; 203—distal inner cambered surface; 2031—inner end of distal inner cambered surface; 2032—outer end of distal inner cambered surface; 204—distal bending arc; 2041—inner end of distal bending arc; 2042—outer end of distal bending arc; and 205—distal outer cambered surface;

300—waist portion;
400—flow blocking membrane;
500—stabilizing wire;
600—septum primum of interatrial septum; and
700—septum secundum of interatrial septum.

DETAILED DESCRIPTION

In order to make the object, technical solutions, and advantages of the embodiments of the present invention clearer, the technical solutions in the embodiments of the present application will be clearly and completely described below. It should be noted that the terms to be described later are defined in consideration of functions in the present invention and may be different according to the intention or convention of a user or an operator. Therefore, the definitions of such terms should be defined based on the whole content of this specification.

For example, orientation or positional relationships indicated by the terms "center", "upper", "lower", "left", "right", "vertical", "horizontal", "inner", "outer", and the like are based on the orientation or positional relationships shown in the drawings, and are intended only to facilitate and simplify the description of the present invention, and are not intended to indicate or imply that the apparatus or element referred to must have a particular orientation, constructed and operated in a particular orientation, and therefore are not to be construed as limitations of the present invention. In addition, the terms "first", "second", and "third" are used for descriptive purposes only and are not to be construed as indicating or implying relative importance.

In the description of the present invention, it should be noted that, unless otherwise explicitly stated or limited, the terms "mounted", "communicated", and "connected" are to be construed broadly, such as fixedly connected, detachably connected, integrally connected, mechanically connected, electrically connected, directly connected, indirectly connected through an intermediate medium, and communicated between two elements. The specific meanings of the above-mentioned terms in the present invention may be understood by a person skilled in the art according to specific circumstances.

In addition, the technical features involved in different implementations of the present invention described below may be combined with each other as long as they do not conflict with each other.

In the related art, the occluder is of an integrally formed mesh structure, including a proximal disc surface, a waist portion, and a distal disc surface. After implantation, the waist portion passes through the tissue septum, and the proximal disc surface and the distal disc surface are arranged at two sides of the tissue septum for occluding the defect. However, due to poor compliance and recovery of the occluder, especially a biodegradable occluder, the proximal disc surface and/or the distal disc surface are easily deformed. Thus, after the occluder is released, the proximal disc surface and the distal disc surface cannot fit well to the left and right sides of the cardiac septal defect position, resulting in a poor occluding effect and even causing a risk of residual blood shunts.

Based on the analysis and discovery of the above-mentioned problems, the present application is proposed.

The present application provides an occluder, including a distal disc, a waist portion, and a proximal disc.

The proximal disc includes a proximal disc surface. A proximal bending area is formed at a circumference of the proximal disc surface and partially or completely bent towards the distal disc. The proximal bending area surrounds an edge of the distal disc, and a stabilizing wire is further threaded through a free end of the proximal bending area and able to tighten the free end of the proximal bending area towards the waist portion.

The proximal disc of the occluder of the present application has the proximal bending area. Based on the provision of the proximal bending area, after the occluder is implanted in the body, the proximal bending area of the proximal disc can surround the distal disc, and the proximal bending area is bent towards the distal disc. Therefore, the free end of the proximal bending area, i.e., the edge of the proximal bending area, forms a closure with an opening pointing towards the distal disc. One or more loops of stabilizing wire that may be retracted (by adjusting a length of the stabilizing wire at the free end of the bending area, e.g., tightening one end of the stabilizing wire for knotting and fixing) are threaded through the free end (i.e., closure) of the proximal bending area. Therefore, when the stabilizing wire locks the proximal disc surface, a centripetal force in the bending area of the proximal disc surface may be enhanced, and a buckling force of the proximal disc surface towards the waist portion may be enhanced.

In the present application, the proximal disc is provided with two regions, i.e., the proximal disc surface and the proximal bending area. The proximal disc surface relatively forms a subsidence area, and the proximal bending area is provided as a part mainly used for providing a locking force so that the recovering effect of the shape of the proximal disc surface may be increased. Specifically, the bending area formed by the proximal bending area may increase a fitting length of the proximal disc to a tissue surface, enhance the fitting and occluding effect, promote rapid endothelialization, and avoid residual shunts. The stabilizing wire is provided so that the proximal bending area may provide a centripetal force to the septal tissue, ensuring that the occluder can stably maintain the design shape and size for a long time after implantation, thereby always fitting to the interatrial septum stably. Meanwhile, the buckling and surrounding pattern of the proximal bending area of the proximal disc to the distal disc may further ensure that the occluder can clamp and fit the septal tissue after implantation.

In some optional embodiments, a diameter of the proximal disc is greater than a diameter of the distal disc; the distal disc includes a distal disc surface, and a distal bending area is formed at a circumference of the distal disc surface; the distal bending area is provided opposite to the proximal bending area, and a free end of the distal bending area (i.e., an outer cambered surface of the distal bending area) extends into the proximal bending area. In these embodiments, the distal disc is also provided with two regions, i.e., the distal disc surface and the distal bending area. The distal bending area is provided opposite to the proximal bending area, and the free end of the distal bending area extends into the proximal bending area so as to form a pattern in which the proximal disc surrounds the distal disc, and the proximal disc and the distal disc are buckled to each other. The distal bending area and the proximal bending area of the occluder are both buckled towards the waist portion in a locked state of the stabilizing wires. The buckling and surrounding pattern of the proximal disc surface and the distal disc surface ensures that the occluder can maximally clamp and fit the atrial septal tissue of the heart after implantation.

In some optional embodiments, the proximal bending area includes a proximal outer cambered surface extending from the circumference of the proximal disc surface; a distance between an inner end of the proximal outer cambered surface and an axis of the waist portion is less than a distance between an outer end of the proximal outer cambered surface and the axis of the waist portion; the stabilizing wire is threaded through the outer end of the proximal outer cambered surface. In these embodiments, a longitudinal profile of the proximal bending area is generally in the form of a ramp having the free end extending away from the waist portion. When the stabilizing wire on the edge of the proximal outer cambered surface is tightened, the ramp can generate a centripetal force on the proximal disc to tighten towards the waist portion, thereby enhancing the buckling force of the proximal disc surface towards the waist portion and enhancing the rebound effect of the proximal disc surface.

In some optional embodiments, the proximal bending area bulges away from the distal disc and includes a proximal inner cambered surface, a proximal bending arc, and the proximal outer cambered surface which are connected in sequence; an inner end of the proximal inner cambered surface is connected to the proximal disc surface, and the stabilizing wire is threaded through the outer end of the proximal outer cambered surface; the distance between the inner end of the proximal outer cambered surface and the axis of the waist portion is less than the distance between the outer end of the proximal outer cambered surface and the axis of the waist portion. Specifically, the proximal inner cambered surface, the proximal bending arc, and the proximal outer cambered surface are connected in sequence from inside to outside.

In these embodiments, the longitudinal profile of the proximal bending area is generally "V"-shaped, and the free end of the proximal outer cambered surface extends obliquely outward away from the waist portion. That is, the proximal outer cambered surface forms a ramp with respect to the proximal disc surface. When the stabilizing wire on the edge of the proximal outer cambered surface is tightened, the ramp can generate a centripetal force on the proximal disc to tighten towards the waist portion, thereby enhancing the buckling force of the proximal disc surface towards the waist portion and enhancing the rebound effect of the proximal disc surface. Meanwhile, the proximal inner cambered surface is provided so that a bending arc is formed between the proximal inner cambered surface and the proximal outer cambered surface, thereby increasing the fitting length of the proximal disc to the tissue surface, and further enhancing the fitting and occluding effect.

In some optional embodiments, a supplementary angle α of an included angle between the proximal outer cambered surface and the proximal disc surface is in a range of greater than 90 degrees and less than 170 degrees. Preferably, the supplementary angle α of the included angle between the proximal outer cambered surface and the proximal disc surface is in a range of greater than 90 degrees and less than 150 degrees.

Further, when the stabilizing wire tightens the proximal bending area, an arc of the proximal bending arc is less than or equal to 90 degrees, and the supplementary angle a of the included angle between the proximal outer cambered surface and the proximal disc surface is in a range of greater than 90 degrees and less than 120 degrees. In these embodiments, when the supplementary angle α of the included angle between the proximal outer cambered surface and the proximal disc surface is in the range of greater than 90 degrees and less than 170 degrees, the clamping and buckling effect of the disc surface may be ensured. When the supplementary angle α is less than 90 degrees or greater than 170 degrees, the centripetal force cannot be generated or the centripetal force is too small, and the clamping and buckling effect is poor.

In some optional embodiments, a projected length of the proximal outer cambered surface in an axial direction of the proximal disc surface is greater than or equal to 1 mm, and a projected length of the proximal outer cambered surface in a radial direction of the proximal disc surface is less than a half of the diameter of the proximal disc. In these embodiments, the reason for limiting the projected length of the proximal outer cambered surface with respect to the axial direction of the proximal disc surface and the projected length of the proximal outer cambered surface with respect to the radial direction of the proximal disc surface is that the applicant has found through several inventive studies that if the projected length of the proximal outer cambered surface in the radial direction of the proximal disc surface has a range of greater than a half of the diameter of the proximal disc, the disc surface will be easily flanged and unable to recover. If the projected length of the proximal outer cambered surface in the axial direction of the proximal disc surface is too short, the disc surface tends to be flat, and the clamping effect is poor.

In some optional embodiments, the distal bending area includes a distal outer cambered surface extending from the circumference of the distal disc surface; a distance between an inner end of the distal outer cambered surface and the axis of the waist portion is less than the distance between the outer end of the proximal outer cambered surface and the axis of the waist portion; the stabilizing wire is threaded through the outer end of the distal outer cambered surface.

Preferably, the distal bending area is bent towards the proximal disc and protrudes, including a distal inner cambered surface, a distal bending arc, and the distal outer cambered surface which extend from the circumference of the distal disc surface in sequence; an inner end of the distal inner cambered surface is connected to the distal disc surface; a distance between an inner end of the distal outer cambered surface and the axis of the waist portion is greater than a distance between an outer end of the distal outer cambered surface and the axis of the waist portion; the free end of the distal outer cambered surface extends into the proximal bending area. In these embodiments, a structure of the distal bending area is the same as that of the proximal bending area, thereby further enhancing the occluding effect of the occluder.

In some optional embodiments, a supplementary angle β of an included angle between the distal outer cambered surface and the distal disc surface is in a range of greater than 90 degrees and less than 170 degrees. Preferably, the supplementary angle B of the included angle between the distal outer cambered surface and the distal disc surface is in a range of greater than 90 degrees and less than 150 degrees. Further, when a stabilizing wire tightens the distal bending area, an arc of the distal bending arc is less than or equal to 90 degrees, and the included angle between the distal outer cambered surface and an extension surface of the distal disc surface is in a range of greater than 90 degrees and less than 120 degrees.

In some optional embodiments, a projected length of the distal outer cambered surface in an axial direction of the distal disc surface is greater than or equal to 1 mm, and a projected length of the distal outer cambered surface in a radial direction of the distal disc surface is in a range of less than a half of the diameter of the distal disc.

In some optional embodiments, a stabilizing wire is also threaded through the free end of the distal bending area, and the stabilizing wire includes one or more loops. Preferably, the stabilizing wires are threaded through the outer end of the proximal outer cambered surface and the outer end of the distal outer cambered surface. In these embodiments, a stabilizing wire may also be provided at the edge of the distal bending area. The stabilizing wire here serves to tighten the distal bending area so that the distal disc has a locking force towards the waist portion so as to enhance the fitting of the distal disc to the tissue surface. Meanwhile, the stabilizing wire may also partially adjust the size of the occluder and adjust the size and shape of the disc surface of the occluder by tightening or loosening and then fixing and knotting, thereby adapting to the atrial septa with different sizes and shapes. Preferably, the stabilizing wire is woven up and down along woven meshes at the edge of the proximal bending area or the distal bending area, with at least one mesh spaced apart.

In some optional embodiments, an inner wall of the distal disc, an inner wall of the proximal disc, and a position between the proximal disc and the distal disc are covered with flow blocking membranes. The flow blocking effect of the occluder may be enhanced by adding the flow blocking membranes on the proximal disc surface, the distal disc surface, and the waist portion of the occluder.

In some optional embodiments, the proximal disc, the waist portion, and the distal disc are all made of degradable wires, and the occluder is further provided with a developing mark. Preferably, the developing mark is a platinum wire or a platinum ring. In these embodiments, the occluder is made of a degradable material so that it is flexible and easy to deform and fit while avoiding wear. The developing mark is provided so that an operator may clearly determine whether the occluder is locked when occluding in the surgical imaging process so as to perform a visual operation, thereby increasing the efficiency of the surgery.

In order to understand the occluder provided by the embodiments of the present disclosure more clearly, specific embodiments of the present disclosure will now be described with reference to the accompanying drawings, in which the thickness of the lines or the size of the structural elements shown in the drawings, etc. may be shown in an exaggerated form for clarity and convenience of the description.

Example 1

Figure 1:
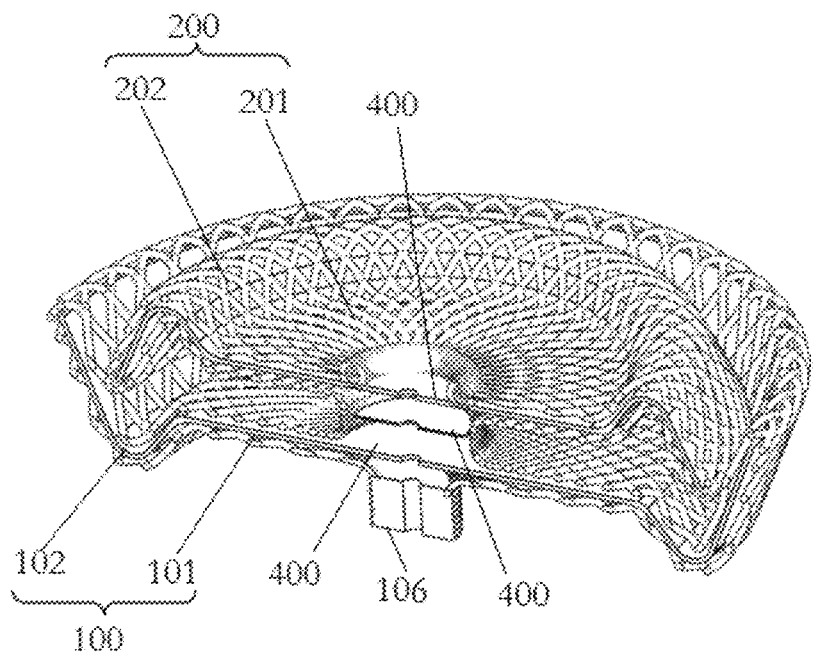
FIG. 1 is a schematic diagram of a part of a structure of an occluder after being cut along a diameter according to an embodiment of the present invention.

In the present application, the proximal end is defined as an end close to the operator during the surgical operation, the distal end is defined as an end away from the operator during the surgical operation, and the orientations of FIGS. 1-7 are identical in the present application. The inner and outer sides are referenced to the waist portion, a side close to the waist portion in the radial direction is defined as the inner side, and a side away from the waist portion in the radial direction is defined as the outer side. Referring to FIG. 1, this embodiment provides an occluder made of a degradable material, including a framework and flow blocking membranes 400. The framework is a closed mesh basket woven from a single degradable wire and is flexible and easy to deform and fit. The closed mesh basket is heat-shaped into a structure of two discs and a waist through a mould, specifically including a proximal disc 100, a distal disc 200, and a waist portion 300 connecting the proximal disc 100 and the distal disc 200. Each of an inner wall of the proximal disc 100, an inner wall of the distal disc 200, and a position between the proximal disc 100 and the distal disc 200 is covered with at least one layer of flow blocking membrane 400, and the material of the flow blocking membrane 400 may be selected as a degradable material. In the present application, the degradable materials involved may include amorphous polylactic acid, levorotatory polylactic acid, dextrorotatory polylactic acid, polydioxanone, polycaprolactone, polyglycolic acid, or a polylactic acid-glycolic acid copolymer. In this embodiment, one or more blends of polydioxanone, polycaprolactone, polyglycolic acid, the polylactic acid-glycolic acid copolymer or amorphous polylactic acid, levorotatory polylactic acid, and dextrorotatory polylactic acid are preferred. The structure of the flow blocking membrane 400 may be a spunlace non-woven fabric, a needle-punched non-woven fabric, a spun-bonded non-woven fabric, a heat-bonded non-woven fabric, a wet-process non-woven fabric, a woven fabric, or an electrostatic spinning fiber membrane. The number of layers of the flow blocking membrane 400 may be 2-6 layers, the flow blocking membrane 400 is sutured and fixed in the framework of the occluder through a suture, and multiple layers of the flow blocking membrane 400 may increase the occluding effect. In addition, in order to facilitate the visual operation of the operator so that the operator may clearly determine whether the occluder is locked when occluding in the surgical imaging process, a developing mark (not shown in the figures) may also be sewn on the flow blocking membrane 400, and the developing mark may be a platinum wire or a platinum ring. A closure of the closed mesh basket is usually located in the center of the proximal disc 100, and a fixing rivet 106 is provided at the closure of the closed mesh basket. The fixing rivet 106 is connected to an external delivery apparatus to facilitate implantation of the occluder in the patient.

Figure 3:
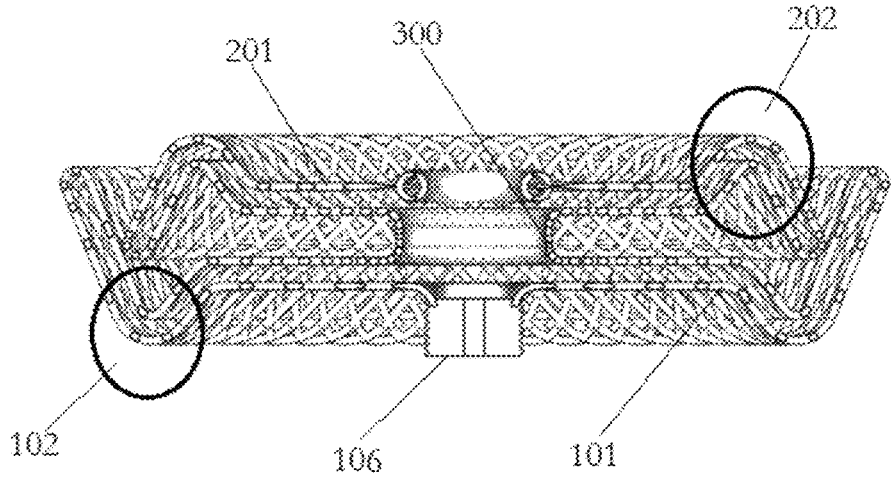
FIG. 3 is a cross-sectional view of an occluder after being cut along a diameter according to an embodiment of the present invention.
Figure 4A:
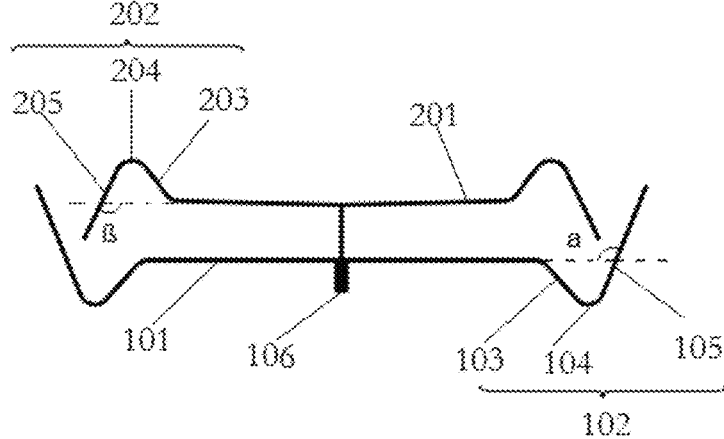
FIGS. 4A-4C are outline schematic diagrams of the occluder of FIG. 3 in a natural state.
Figure 4B:
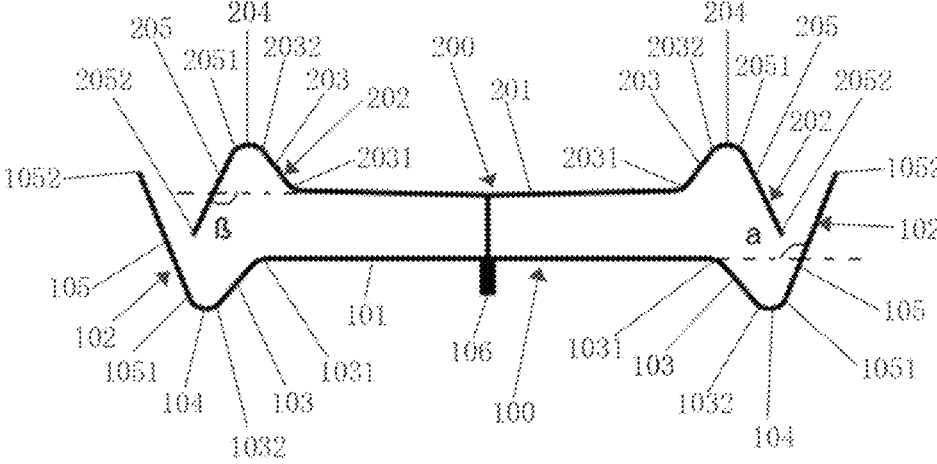
Figure 4C:
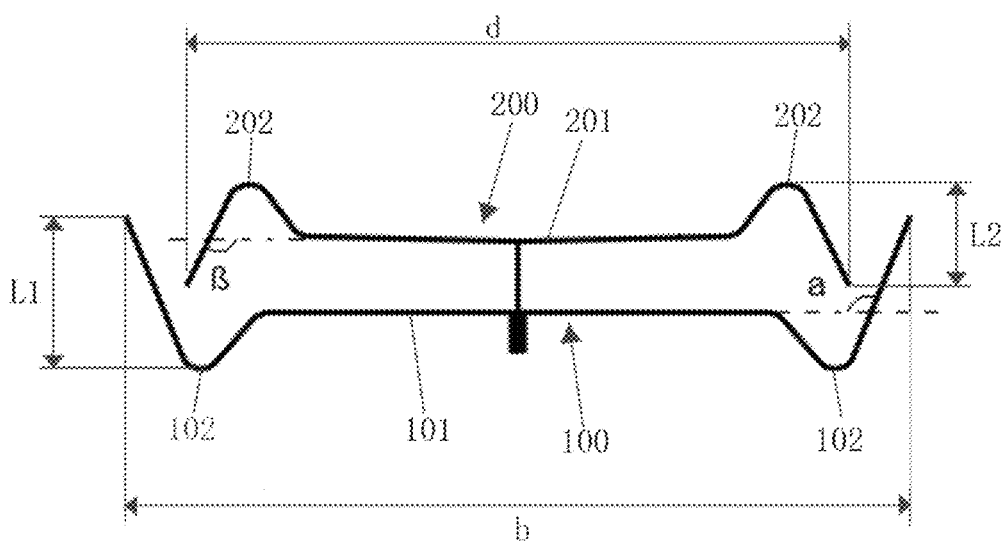
Figure 5:
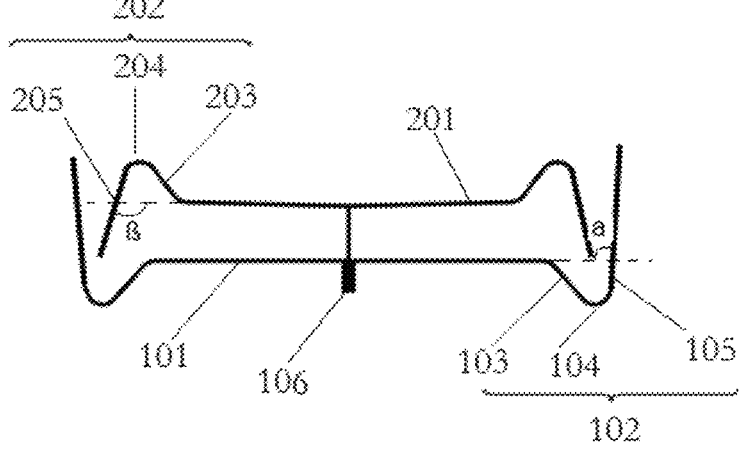
FIG. 5 is an outline schematic diagram of the occluder of FIG. 3 in a locked state.

In the present disclosure, referring to FIGS. 3-5, a diameter of the proximal disc 100 is greater than or equal to a diameter of the distal disc 200. The proximal disc 100 includes a proximal disc surface 101 and a proximal bending area 102, and an edge of the proximal bending area 102 is higher than an edge of the distal disc 200, forming a surrounding pattern in which the proximal disc 100 surrounds the distal disc 200. The proximal bending area 102 extends from a circumference of the proximal disc surface 101, and it is partially or completely bent towards the distal disc 200 and protrudes. It can be understood that the proximal disc 100 includes a subsidence area and a bending area. The proximal disc surface 101 constitutes the subsidence area with a subsidence depth of 0.5-3 mm, and the subsidence area may increase the recovering effect of the shape of the proximal disc 100. The proximal bending area 102 constitutes the bending area, and the bending area may extend the length of the proximal bending area 102 and increase a fitting length of the proximal disc 100 to a tissue surface, thereby enhancing the fitting and occluding effect. Referring to FIGS. 4A-4C, the proximal bending area 102 includes a proximal inner cambered surface 103, a proximal bending arc 104, and a proximal outer cambered surface 105 which extend from the edge of the proximal disc surface 101 in sequence. The proximal bending arc 104 protrudes from the proximal disc surface 101 in a direction away from the waist portion 300, and an arc of the proximal bending arc 104 is 30 degrees to 120 degrees. The proximal inner cambered surface 103 and the proximal outer cambered surface 105 each form a ramp with respect to the proximal disc surface 101. A distance between an inner end 1051 of the proximal outer cambered surface 105 and an axis of the waist portion 300 is less than a distance between an outer end 1052 of the proximal outer cambered surface 105 and the axis of the waist portion 300. That is, a free end of the proximal outer cambered surface 105 is diverged outwards with respect to the waist portion 300. A supplementary angle $\alpha$ of an included angle between the proximal outer cambered surface 105 and the proximal disc surface 101 is in a range of greater than 90 degrees and less than 170 degrees. In this embodiment, the supplementary angle $\alpha$ of the included angle between the proximal outer cambered surface 105 and the proximal disc surface 101 is in a range of greater than 90 degrees and less than 150 degrees. A projected length L1 of the proximal outer cambered surface 105 in an axial direction of the proximal disc surface 101 is greater than or equal to 1 mm, and a projected length of the proximal outer cambered surface in a radial direction of the proximal disc surface 101 is less than a half of a diameter b of the proximal disc 100. Referring specifically to FIG. 4B, the proximal inner cambered surface 103 includes an inner end 1031 of the proximal inner cambered surface and an outer end 1032 of the proximal inner cambered surface. The proximal outer cambered surface 105 includes the inner end 1051 of the proximal outer cambered surface and the outer end 1052 of the proximal outer cambered surface. The proximal inner cambered surface 103, the proximal bending arc 104, and the proximal outer cambered surface 105 are connected in sequence from inside to outside. More specifically, the inner end 1031 of the proximal inner cambered surface is connected to the proximal disc surface 101, the outer end 1032 of the proximal inner cambered surface is connected to one end of the proximal bending arc 104, the other end of the proximal bending arc 104 is connected to the inner end 1051 of the proximal outer cambered surface, and the outer end 1052 of the proximal outer cambered surface is at an outer edge of the proximal disc 200. Furthermore, the proximal inner cambered surface 103 extends gradually from inside to outside in a direction away from the inner disc surface 201 (i.e., extends proximally in an inside to outside direction), and the proximal outer cambered surface 105 extends gradually from inside to outside in a direction close to the distal disc surface 201 (i.e., extends distally in an inside to outside direction).

With continued reference to FIG. 4B, the distal inner cambered surface 203 includes an inner end 2031 of the distal inner cambered surface and an outer end 2032 of the distal inner cambered surface, and the distal outer cambered surface 205 includes an inner end 2051 of the distal outer cambered surface and an outer end 2052 of the distal outer cambered surface. The distal inner cambered surface 203, a distal bending arc 204, and the distal outer cambered surface 205 are connected in sequence from inside to outside. More specifically, the inner end 2031 of the distal inner cambered surface is connected to the distal disc surface 201, the outer end 2032 of the distal inner cambered surface is connected to one end of the distal bending arc 204, the other end of the distal bending arc 204 is connected to the inner end 2051 of the distal outer cambered surface, and the outer end 2052 of the distal outer cambered surface is at an outer edge of the distal disc 200. Furthermore, the distal inner cambered surface 203 extends gradually from inside to outside in a direction away from the proximal disc surface 101 (i.e., extends distally in an inside to outside direction), and the distal outer cambered surface 205 extends gradually from inside to outside in a direction close to the proximal disc surface 101 (i.e., extends proximally in an inside to outside direction).

It should be noted that the occluder in FIGS. 4A, 4B, and 4C is the same occluder, and FIGS. 4A, 4B, and 4C are provided for ease of reading and understanding.

Figure 2:
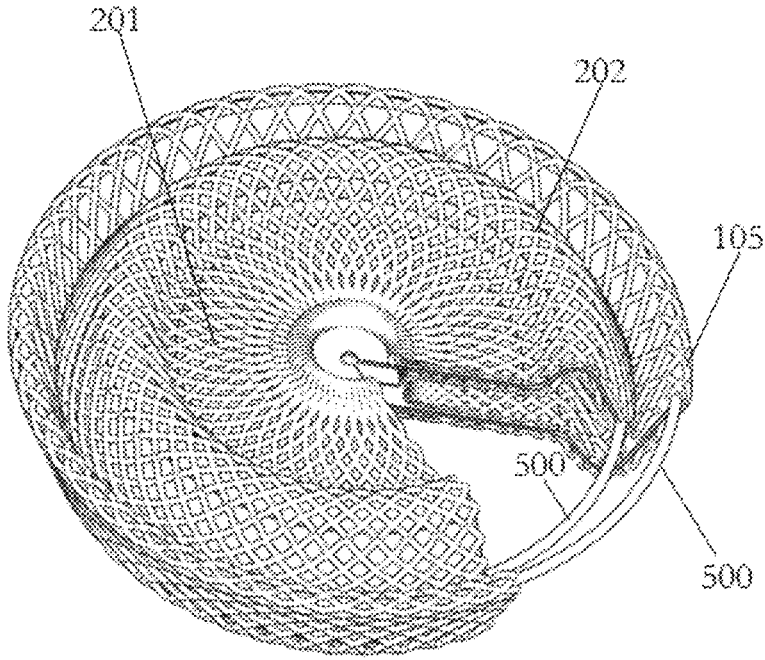
FIG. 2 is a schematic diagram of a positional relationship of stabilizing wires in an occluder according to an embodiment of the present invention.

Referring to FIG. 2, in this embodiment, a stabilizing wire 500 is threaded through the outer end of the proximal outer cambered surface 105, and the stabilizing wire 500 includes one or more loops. Referring to FIGS. 4A-6, the stabilizing wire 500 is tightened so that the diameter of the proximal disc 101 is reduced, the arc of the proximal bending arc 104 is reduced, and the supplementary angle α of the included angle between the proximal outer cambered surface 105 and the proximal disc surface 101 is reduced to 90-120°. After the stabilizing wire 500 locks the proximal disc 101, the centripetal force of the proximal outer cambered surface 105 is enhanced, and the buckling force of the proximal disc 100 towards the waist portion 300 is enhanced so that the proximal disc 100 is more fit to the tissue surface, and the rebound effect of the proximal disc 100 is enhanced. Meanwhile, the stabilizing wire 500 may also partially adjust the size of the occluder and adjust the size and shape of the disc of the occluder by tightening or loosening and then fixing and knotting, thereby adapting to tissue defects with different sizes and shapes. When entering the proximal bending area 102, the stabilizing wire is preferably woven up and down along woven meshes at the edge of the proximal bending area 102, with at least one mesh spaced apart.

In this embodiment, the proximal disc 100 is provided with two regions, i.e., the proximal disc surface 101 and the proximal bending area 102. The proximal disc surface 101 relatively forms a subsidence area, and the proximal bending area 102 is provided as a part mainly used for providing a locking force so that the recovering effect of the shape of the proximal disc surface 101 may be increased. Specifically, the bending area formed by the proximal bending area 102 may increase a fitting length of the proximal disc 100 to a tissue surface, enhance the fitting and occluding effect, promote rapid endothelialization, and avoid residual shunts. The stabilizing wire 500 is provided so that the proximal bending area 102 may provide a centripetal force to the septal tissue, ensuring that the occluder can stably maintain the design shape and size for a long time after implantation, thereby always fitting to the interatrial septum stably. Meanwhile, the buckling and surrounding pattern of the proximal bending area 102 of the proximal disc 100 to the distal disc 200 may further ensure that the occluder can clamp and fit the septal tissue after implantation.

Example 2

Referring to FIG. 7, different from embodiment 1, in this embodiment, the proximal bending area 102 includes a proximal outer cambered surface 105 extending from the circumference of the proximal disc surface 101. A distance between a proximal end of the proximal outer cambered surface 105 and the axis of the waist portion 300 is less than a distance between a distal end of the proximal outer cambered surface 105 and the axis of the waist portion 300. A stabilizing wire 500 is threaded through the distal end of the proximal outer cambered surface 105. In this embodiment, a longitudinal profile of the proximal bending area 102 is generally in the form of a ramp having the free end extending away from the waist portion 300. When the stabilizing wire 500 on the circumference of the proximal outer cambered surface 105 is tightened, the ramp can generate a centripetal force on the proximal disc 100 to tighten towards the waist portion 300, thereby enhancing the buckling force of the proximal disc surface 101 towards the waist portion 300 and enhancing the rebound effect of the proximal disc surface 101.

Example 3

Referring to FIGS. 4A and 4B, in this embodiment, the distal disc 200 is also provided with a bending area, that is, the distal disc 200 includes a distal disc surface 201 and a distal bending area 202. The distal bending area 202 extends from the circumference of the distal disc surface 201. The distal bending area 202 is provided opposite to the proximal bending area 102, and a free end of the distal bending area 202 extends into the proximal bending area 102 so as to form a surrounding pattern in which the proximal disc surface 101 surrounds the distal disc surface 201. The distal bending area 202 and the proximal bending area 102 of the occluder are both buckled towards the waist portion 300 in a state where the stabilizing wire 500 in the proximal bending area 102 is locked. The buckling and surrounding pattern of the proximal disc surface 101 and the distal disc surface 201 ensures that the occluder can maximally clamp and fit the atrial septal tissue of the heart after implantation.

The structure of the distal bending area 202 is the same as that of the proximal bending area 102. For example, referring to FIGS. 4A and 4B, the longitudinal profile may be generally in an inverted "V" shape, i.e., the distal bending area 102 is bent towards the proximal disc 100 and protrudes. The distal bending area 202 includes a distal inner cambered surface 203, a distal bending arc 204, and a distal outer cambered surface 205 which extend from the circumference of the distal disc surface 201 in sequence, and a free end of the distal outer cambered surface 205 extends obliquely outward away from the waist portion 300. That is, a distance between the inner end 2051 of the distal outer cambered surface 205 and the axis of the waist portion 300 is greater than a distance between the outer end 2052 of the distal outer cambered surface 205 and the axis of the waist portion 300. Each of the distal outer cambered surface 205 and the distal inner cambered surface 203 forms a ramp with respect to the distal disc surface 201, but the distal outer cambered surface 205 is a ramp with its proximal end diverging outwards with respect to the waist portion 300. The free end of the distal outer cambered surface 205 extends into the proximal bending area 102 so as to form a surrounding pattern with the proximal bending area 102. The structure of the distal disc 200 may also include only a distal outer cambered surface 205 extending from the circumference of the distal disc surface 201. The distance between the inner end 2051 of the distal outer cambered surface 205 and the axis of the waist portion 300 is greater than the distance between the outer end 2052 of the distal outer cambered surface 205 and the axis of the waist portion 300. A stabilizing wire 500 is threaded through the outer end 2052 of the distal outer cambered surface 205, i.e., the longitudinal profile of the proximal bending area 102 is generally in the form of a ramp having the free end extending away from the waist portion 300. No matter what kind of structure exists, a supplementary angle β of an included angle between the distal outer cambered surface 205 and the distal disc surface 201 is in a range of greater than 90 degrees and less than 170 degrees. In this embodiment, the supplementary angle β of the included angle between the distal outer cambered surface 205 and the distal disc surface 201 is in a range of greater than 90 degrees and less than 150 degrees to ensure the clamping and buckling effect of the distal disc surface 201 and avoid the problem that the included angle is too large or too small, which could result in insufficient centripetal force or the inability to generate centripetal force. A projected length L2 of the distal outer cambered surface 205 in an axial direction of the distal disc surface 201 is greater than or equal to 1 mm. In order to avoid the problem that the distal disc 200 tends to be flat and the clamping effect is poor, a projected length of the distal outer cambered surface in a radial direction of the distal disc surface 201 is in a range of less than a half of the diameter d of the distal disc 200 to avoid the distal disc 200 from being flanged and unable to recover.

Example 3

Referring to FIG. 2, in this embodiment, a stabilizing wire 500 is also threaded through the free end of the distal bending area 202, i.e., the stabilizing wires 500 are threaded through the distal end of the proximal outer cambered surface 105 and the proximal end of the distal outer cambered surface 205. The stabilizing wire 500 provided at the free end of the distal bending area 202 may play the role of tightening the distal bending area 202 so that the distal disc 200 has a locking force towards the waist portion 300 so as to enhance the fitting of the distal disc 200 to the tissue surface. When the stabilizing wire 500 tightens the distal bending area 202, the arc of the distal bending arc 204 is less than or equal to 90 degrees, and the included angle between the distal outer cambered surface 205 and an extension surface of the distal disc surface 201 is in a range of greater than 90 degrees and less than 120 degrees.

Figure 6:
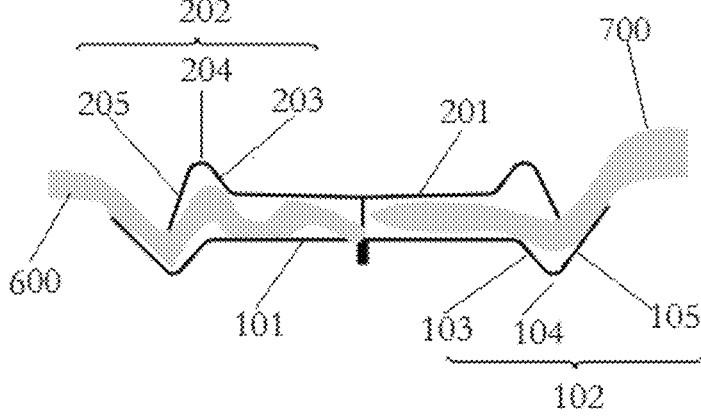
FIG. 6 is a schematic structural diagram of an occluder after being released at a position of a PFO according to an embodiment of the present invention.

FIG. 6 is an occluding schematic diagram showing the implantation of the occluder in the PFO. In FIG. 6, a septum primum 600 of the interatrial septum and a septum secundum 700 of the interatrial septum are not completely fused, leaving an oblique defect in the middle. The occluder of the present application is implanted to clamp the atrial septal tissue. The distal disc 200 and the proximal disc 100 may closely fit to the atrial septal tissue, promoting rapid endothelialization and avoiding residual shunts. The stabilizing wire 500 can ensure that the occluder may stably maintain the design shape and size for a long time after implantation, thereby always fitting to the interatrial septum stably.

The above are only preferred embodiments of the present invention and are not intended to limit the scope of the present invention. Any modifications, equivalents, improvements, etc. made within the spirit and principles of the present invention should be included within the scope of the present invention.

What is claimed is:

1. An occluder, comprising a distal disc, a waist portion and a proximal disc formed in sequence, wherein:
   the waist portion connects the proximal disk to the distal disk;

the proximal disc comprises a proximal disc surface,
   a proximal bending area bent toward the distal disc is formed at a circumference of the proximal disc surface,
   the proximal bending area surrounds an edge of the distal disc, and
   a stabilizing wire comprising one or more loops is threaded through a free end of the proximal bending area and the stabilizing wire is able to tighten the free end of the proximal bending area towards the waist portion.

2. The occluder according to claim 1, wherein:
   a diameter of the proximal disc is greater than a diameter of the distal disc,
   the distal disc comprises a distal disc surface,
   a distal bending area arranged opposite to the proximal bending area is formed at a circumference of the distal disc surface, and
   a free end of the distal bending area extends into the proximal bending area.

3. The occluder according to claim 1, wherein:
   the proximal bending area comprises a proximal outer cambered surface extending from the circumference of the proximal disc surface,
   a distance between an inner end of the proximal outer cambered surface and an axis of the waist portion is less than a distance between an outer end of the proximal outer cambered surface and the axis of the waist portion, and
   the stabilizing wire is threaded through the outer end of the proximal outer cambered surface.

4. The occluder according to claim 1, wherein:
   the proximal bending area bulges away from the distal disc and comprises a proximal inner cambered surface,
   a proximal bending arc and the proximal outer cambered surface connected in sequence,
   an inner end of the proximal inner cambered surface is connected to the proximal disc surface,
   the stabilizing wire is threaded through the outer end of the proximal outer cambered surface, and
   the distance between the inner end of the proximal outer cambered surface and the axis of the waist portion is less than the distance between the outer end of the proximal outer cambered surface and the axis of the waist portion.

5. The occluder according to claim 4, wherein a projected length of the proximal outer cambered surface in an axial direction of the proximal disc surface is greater than or equal to 1 mm, and a projected length of the proximal outer cambered surface in a radial direction of the proximal disc surface is less than a half of the diameter of the proximal disc.

6. The occluder according to claim 1, wherein a supplementary angle α of an included angle between the proximal outer cambered surface and the proximal disc surface is in a range of greater than 90 degrees and less than 170 degrees.

7. The occluder according to claim 1, wherein when the stabilizing wire tightens the proximal bending area, an arc of the proximal bending arc is less than or equal to 90 degrees, and the supplementary angle a of the included angle between the proximal outer cambered surface and the proximal disc surface is in a range of greater than 90 degrees and less than 160 degrees.

8. The occluder according to claim 3, wherein:
   the distal bending area comprises a distal outer cambered surface extending from the circumference of the distal disc surface, a distance between an inner end of the distal outer cambered surface and the axis of the waist portion is greater than the distance between the outer end of the proximal outer cambered surface and the axis of the waist portion, and the stabilizing wire is threaded through the outer end of the distal outer cambered surface.

9. The occluder according to claim 8, wherein:

the distal bending area is bent towards the proximal disc and protrudes, including a distal inner cambered surface, a distal bending arc and the distal outer cambered surface extending from the circumference of the distal disc surface in sequence, a distance between an outer end of the distal outer cambered surface and the axis of the waist portion is greater than a distance between an outer end of the distal outer cambered surface and the axis of the waist portion, and the free end of the distal outer cambered surface extends into the proximal bending area.

10. The occluder according to claim 8, wherein a supplementary angle β of an included angle between the distal outer cambered surface and the distal disc surface is in a range of greater than 90 degrees and less than 170 degrees.

11. The occluder according to claim 10, wherein:

when second a stabilizing wire tightens the distal bending area, an arc of the distal bending arc is less than or equal to 90 degrees, and the supplementary angle β of the included angle between the distal outer cambered surface and an extension surface of the distal disc surface is in a range of greater than 90 degrees and less than 160 degrees, a projected length of the distal outer cambered surface in an axial direction of the distal disc surface is greater than or equal to 1 mm, and a projected length of the distal outer cambered surface in a radial direction of the distal disc surface is less than a half of the diameter of the distal disc.

12. The occluder according to claim 1, characterized in that, wherein a second stabilizing wire is threaded through the free end of the distal bending area, and the second stabilizing wire comprises one or more loops.

13. The occluder according to claim 1, wherein an inner wall of the distal disc, an inner wall of the proximal disc, and a position between the proximal disc and the distal disc are covered with flow blocking membranes.

14. The occluder according to claim 1, wherein the proximal disc, the waist portion, and the distal disc are all made of degradable wires, and the occluder is further provided with a developing mark.

15. The occluder according to claim 14, wherein the developing mark is a platinum wire or a platinum ring.

* * * * *